United States Patent [19]

Ameseder

[11] Patent Number: 5,029,252
[45] Date of Patent: Jul. 2, 1991

[54] APPARATUS FOR DISINFECTION OF LAVATORY OR MEDICAL INSTRUMENTS

[76] Inventor: Anton Ameseder, Löwengartenstrasse 11, CH-9400 Rorschach, Switzerland

[21] Appl. No.: 450,209

[22] Filed: Dec. 12, 1989

[30] Foreign Application Priority Data

Aug. 23, 1989 [EP] European Pat. Off. ......... 89115527.7

[51] Int. Cl.⁵ ................................................ A61L 3/00
[52] U.S. Cl. ............................. 250/455.1; 250/504 R; 422/24
[58] Field of Search ............. 250/455.1, 454.1, 504 R; 422/24, 212; 315/159

[56] References Cited

U.S. PATENT DOCUMENTS

| | | | |
|---|---|---|---|
| 2,814,081 | 11/1957 | Stevenson | 422/24 |
| 3,820,251 | 6/1974 | Abernathy | 422/24 |
| 3,955,922 | 5/1976 | Moulthrop | 422/24 |
| 4,063,890 | 12/1977 | Baron | 422/24 |
| 4,088,445 | 5/1978 | Ellis | 250/455.1 |
| 4,740,706 | 4/1988 | Murdock, III | 422/24 |
| 4,803,364 | 2/1989 | Ritter | 250/504 R |
| 4,806,770 | 2/1989 | Hylton et al. | 250/455.1 |
| 4,906,851 | 3/1990 | Beasley et al. | 250/455.1 |

Primary Examiner—Jack I. Berman
Assistant Examiner—Kiet T. Nguyen
Attorney, Agent, or Firm—Nilsson, Robbins, Dalgarn, Berliner, Carson & Wurst

[57] ABSTRACT

Apparatus for disinfection of lavatory instruments, medical instruments or the like, through ultraviolet radiation, wherein the instruments are arranged within a housing in combination with a mounting plate and irradiated by a light source which generates UV-radiation. The apparatus is designed to achieve the highest possible degree of effectiveness with a shadow-free irradiation of the instruments to be treated with simple manipulation of the apparatus. A receiving vessel with a take-up frame is insertable in the mounting plate, and the housing provided with openings is pivotable and engageable on arms of the mounting plate.

20 Claims, 5 Drawing Sheets

APPARATUS FOR DISINFECTION OF LAVATORY OR MEDICAL INSTRUMENTS

BACKGROUND OF THE INVENTION

The present invention relates to apparatus for disinfection or sterilization of lavatory instruments, medical instruments, or the like, and in particular toothbrushes, through the use of ultraviolet radiation, whereby the instrument (e.g., toothbrush) is arranged in a housing in combination with a mounting or base plate and irradiated by a source of light which generates UV-radiation.

Disinfection, i.e., the rendering harmless of potential causes of illness such as bacteria, has heretofore been effected most commonly using chemical means. Further, it has long been known to sterilize instruments through the effects of heat, for example using an autoclave which operates at temperatures on the order of 120° to 145° C. under steam pressure.

From German Offenlegungsschrift DE-OS 32 09 701 it is also already known to render medical instruments in particular germ free with the aid of UV-radiation. The medical instruments are inserted into slots or grooves in a mounting plate, which is placed into a housing wherein the instruments are sterilized by means of UV-radiation. The complete apparatus is nonetheless relatively complicated to manipulate; further, the apparatus does not permit achievement of an accurate and uniform distribution of the UV-radiation over the total area of disinfection. In addition, the known apparatus is not suitable for the disinfection of toothbrushes.

It is therefore an object of the present invention to provide an apparatus for the disinfection of toilette or medical instruments, and in particular toothbrushes, which is both simple to manipulate and cost efficient, while providing uniform distribution of the UV-radiation.

SUMMARY OF THE INVENTION

In accordance with the present invention, the instruments to be disinfected (e.g., the toothbrushes) are arranged with respect to the mounting plate and the radiation source in a consistently reproduceable manner such that the disinfection area itself is enclosed in a pivotable housing. Through the introduction of the instruments such as toothbrushes to the mounting plate or UV-source by means of a receiving vessel with a take-up frame, a consistently and reproducibly uniform UV-irradiation of the receiving vessel is achieved. Through the enclosure of the receiving vessel with a housing, wherein the instruments such as toothbrushes are placed into openings in the housing, there is provided a disinfection chamber which is easier to manipulate and which exhibits in the direct vicinity of the UV-source a particularly high degree of effectiveness with respect to disinfection of medical instruments and/or toothbrushes.

DETAILED DESCRIPTION OF THE INVENTION

Figure 1:
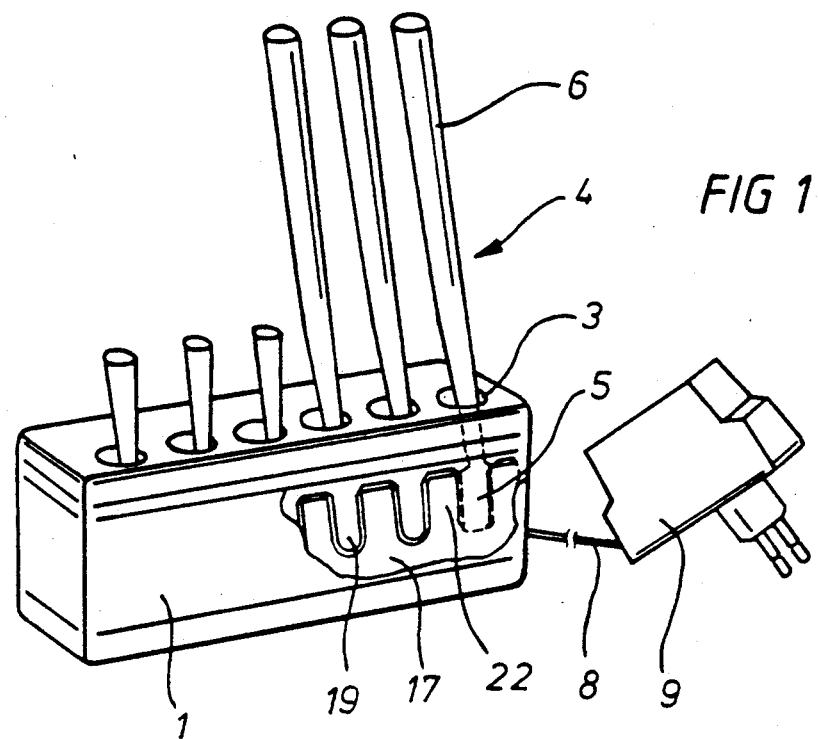
FIG. 1 is a perspective illustration of the inventive apparatus.

The inventive apparatus is particularly suitable for use with toothbrushes, which are often exposed to dust and the warm, moist environment of the bathroom in a drinking glass, often as well together with other objects that may contain germs, such as wet razors and the like. Under such conditions, bacteria may multiply a millionfold on such an exposed toothbrush in a few hours. Through the use of such a toothbrush, the infectious agents are introduced into the mouth, where they may significantly contribute to inflammatory infections of the mouth and throat.

The invention is further useful above all in the medical field. In this context, the invention is useful for disinfection of, e.g., instruments for the cutting of hair, such as razor knives, razor blades, scissors, shear heads for hair cutting apparatus, etc.

In a particularly advantageous embodiment, the mounting plate of the apparatus for disinfection is provided with an aperture for the UV-light source, whereby the receiving vessel with the take-up frame is brought forward to the light source in the manner of a sliding unit or rack. Thereby is achieved in combination with the insertion of the receiving vessel for the instruments an essentially uniform illumination of the area of disinfection with UV-radiation.

It is contemplated that advantageously the sides of the mounting plate are provided with guides or tracks, in which the receiving vessel may be pushed over further tracks. Through insertion of the receiving vessel over tracks in the mounting plate, the receiving vessel is positioned in a simple manner and further may be easily removed from the mounting plate for other purposes, for example cleaning.

The base of the receiving vessel is advantageously troughlike or trenchlike and provided with a drainage opening, through which any cleaning solution on the instruments or toothbrushes can drop off harmlessly.

The troughlike construction of the receiving vessel has the further advantage, that in combination with the enclosing housing there is generated in the lower region of the apparatus an advantageous disinfection area, where there accumulates a certain level of ozone which is additionally useful for disinfection. This level of ozone, which increases with the length of the disinfection process, is in this manner contained in the trough of the receiving vessel in the region of the take-up frame for the medical instruments or toothbrushes, and is prohibited from escaping in particular by the surrounding housing.

Through the provision of a receiving vessel with a trenchlike base, which additionally is surrounded in the region of the mounting plate by a pivotable housing, it is possible according to the present invention to achieve a particularly advantageous UV-disinfection, because due to multiple reflection of the UV-radiation not only in the region of the receiving vessel but also on the housing there is achieved a shadow-free UV-irradiation of the medical instruments or toothbrushes to be disinfected.

In a particularly advantageous embodiment, it is contemplated that the receiving vessel is provided with a highly rifled or contoured wall, which in combination with the interposed take-up frame forms a take-up aperture for instruments or toothbrushes.

In a further advantageous embodiment, there are arranged infrared sensors comprising transmitter and receiver diodes on the mounting plate in a side-by-side arrangement with illumination of the interior region of the housing in the area of the receiving vessel and the openings in the housing. Thereby the UV-radiation source is automatically actuated by the initiation of movement within the housing and/or the receiving vessel, whereby disinfection is initiated.

Through a scientific investigation of the inventive apparatus by the Institute for Hygiene and Medical Microbiology of the University of Bern, the efficacy of the apparatus was established. From an overnight culture of E. coli a suspension containing about $5 \times 10^6$ cells per ml was prepared. A number of toothbrushes were immersed in this cell suspension and then shaken to remove excess liquid containing bacteria. The thus-treated brushes were then either introduced directly into a fresh and sterile culture medium, or first treated for 10 minutes, 20 minutes or 40 minutes in the inventive apparatus under a UV-light source, in every case with a determination of the number of cells in the culture medium. In this manner, it was determined that after 40 minutes, 98% of the cells were killed.

As a result of this investigation, it is therefore advantageous to provide the control device with a counter, whereby the actuated UV-light source is automatically extinguished after a predetermined period of time, for example an hour.

In a further embodiment the control device may also be provided with a thermostat, which will extinguish the actuated UV-light source when a predetermined temperature is exceeded and actuate the light source again when the temperature falls below the predetermined value.

The apparatus for disinfection according to FIGS. 1 and 3-5 comprises a visually attractive housing, advantageously of plastic, in which an ultraviolet ray generating light source 2 is provided. In the present case, it is in the form of a tube.

The housing 1 is provided according to FIG. 1 with a plurality of openings 3, in which the toothbrushes 4 may so be placed, that the brush heads 5 are located within the housing 1 and the handles 6 extend outside the housing 1. The UV-light source 2 is mounted according to FIG. 3 on the mounting plate 7 of the housing 1 and is connected by a wire 8 to a plug 9.

Figure 3:
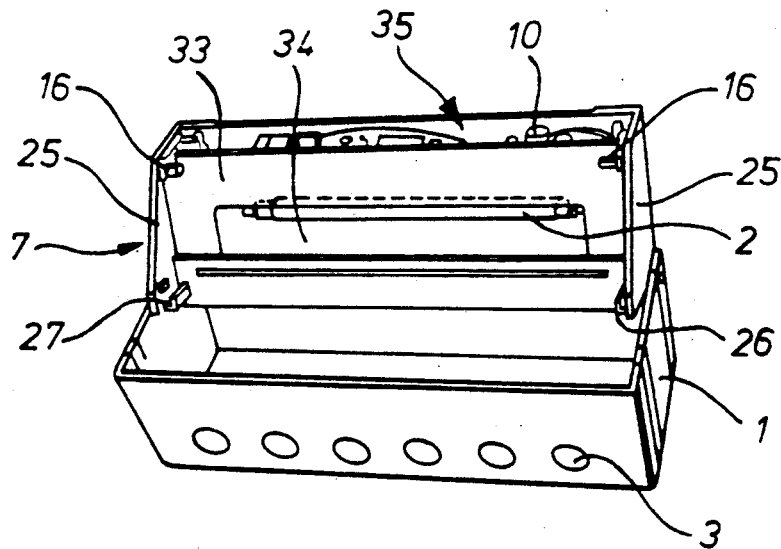
FIG. 3 is a perspective illustration of the mounting plate with the housing opened up.

In FIG. 1 the housing 1 has been pivoted and swung shut on the mounting plate as illustrated in FIG. 3, and toothbrushes 4 comprising a brush head 5 and a handle 6 have been inserted into the openings 3.

In FIG. 1 is further illustrated in a partial arrangement the take-up frame 17, comprising prongs 22 and take-up openings 19 formed thereby, whereby in a take-up opening 19 the brush head 5 of a toothbrush 4 is inserted.

FIG. 3 illustrates the housing 1 swung open and without the receiving vessel 18 and take-up frame 17.

Figure 4:
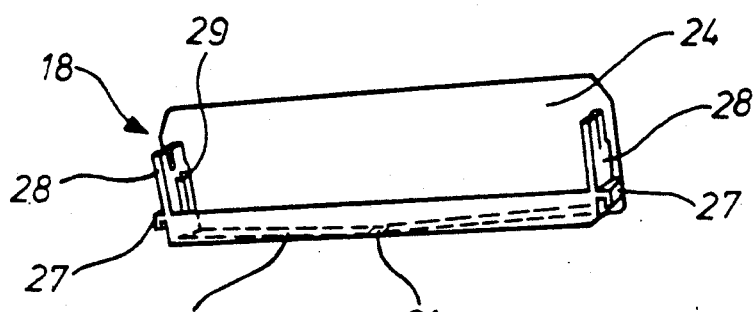
FIG. 4 is the receiving vessel in a perspective illustration.

The mounting plate 7 is provided with side pieces or arms 25, on which tracks 26 are arranged for the receiving vessel 18 according to FIG. 4.

The mounting plate 7 further comprises a wall 33 provided with a light opening 34 for the light source 2 which is situated behind the wall.

On the side of the mounting plate 7 in the upper region of the side walls 26 which run to a point are located sensors 16, in particular infrared sensors, comprising infrared transmitters and infrared receivers.

Figure 9:
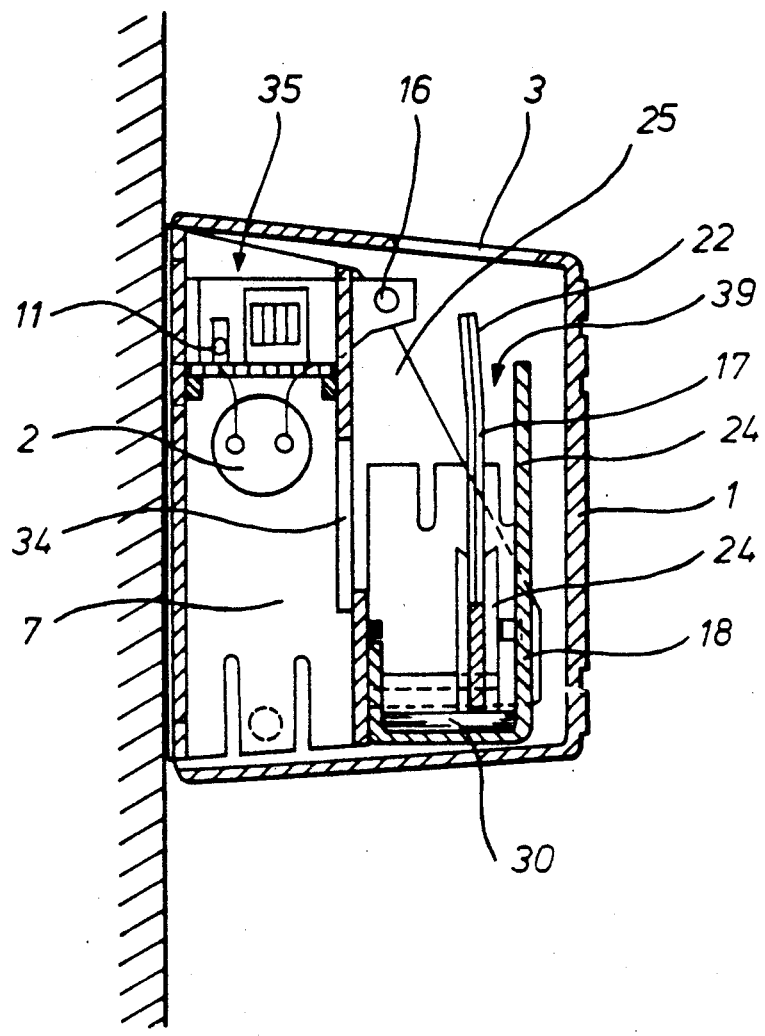
FIG. 9 is a cross-section of the apparatus according to FIG. 1, without inclusion of the inserted toothbrushes.

In FIG. 3 is illustrated also in combination with FIG. 9 a receptacle 35 in the mounting plate 7, where the complete electronics including the control device 10 and the light source 2 can be introduced located on a unitary plate.

Figure 5:
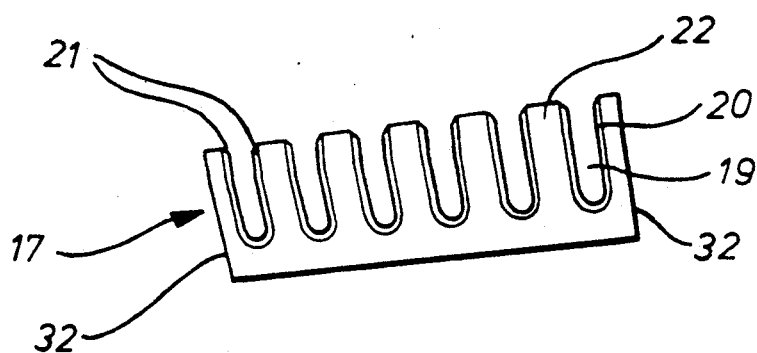
FIG. 5 is a take-up frame in accordance with the present invention.

In FIG. 5 the take-up frame 17 is illustrated, which is taken up in the receiving vessel 18 of FIG. 4 after rotation around 180 degrees.

The take-up frame 17 is provided with rims or ridges 32, which are introduced into the longitudinal tracks 29 of the receiving vessel 18, whereby mounting supports 28 are formed on the receiving vessel 18.

Figure 7:
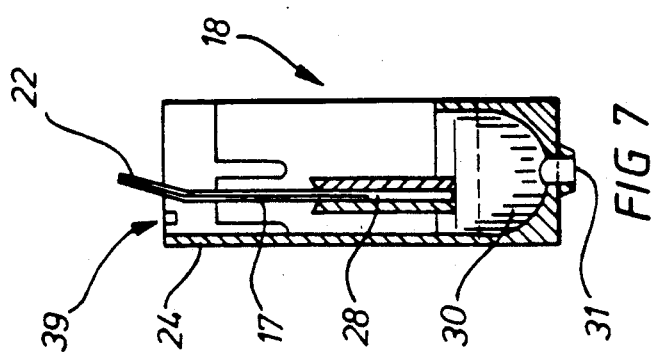
FIG. 7 is a cross-section of the receiving vessel with interposed take-up frame according to FIG. 6.

After the introduction of the take-up frame 17 into the receiving vessel 18, the receiving vessel itself is pushed into the mounting plate 7 according to FIG. 7 in the manner of a slide-in unit, whereby the tracks 27 of the receiving vessel 18 are inserted into the tracks 26 of the mounting plate 7.

With reference to the illustration of FIG. 4, the receiving vessel 18 is rotated around 180 degrees, so that the rear wall 24 of the receiving vessel 18 is arranged opposite the light source 2 and upon insertion of the take-up frame 17 according to FIG. 7 and FIG. 9 there is formed a take-up aperture 39 for instruments or toothbrushes to be introduced.

Figure 6:
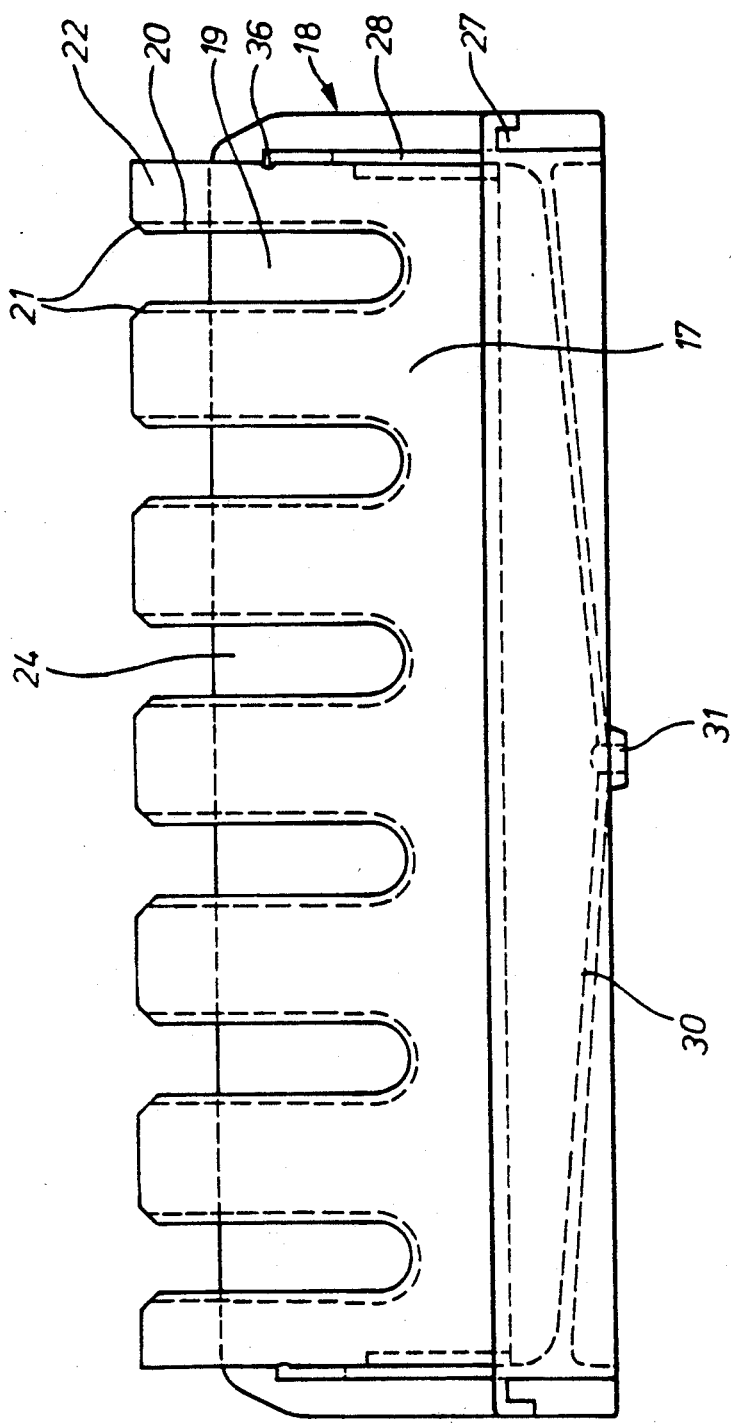
FIG. 6 is a receiving vessel with an interposed take-up frame in an illustration.
Figure 8:
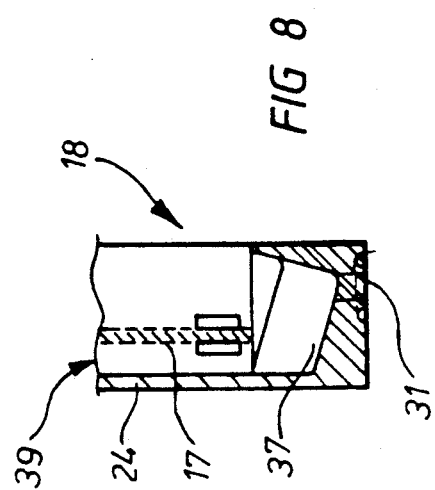
FIG. 8 is a cross-section according to FIG. 6 of another embodiment.

From FIG. 4 in combination with FIG. 6 it is evident that the receiving vessel 18 is constructed in a troughlike form, and in particular according to FIGS. 7 and 8 is seen to form a trough 30 and 37, respectively, provided with an outlet opening 31.

In FIG. 5 it is illustrated, that tracks 20 are formed on the prongs 22 of the take-up frame 17 as well as inlet bevels 21 on the teeth 22, in order to facilitate introduction of instruments, such as toothbrushes.

FIG. 6 illustrates with the same reference numerals the take-up frame 17 inserted into the receiving vessel 18, whereby it is apparent, that on each holder 28 of the receiving vessel 18 there is provided a catch 36, which latches onto the take-up frame 17 by a corresponding indentation or the like.

From FIGS. 7 and 8 it is particularly clear in the cross-section of receiving vessel 18 and take-up frame 17, that in combination with the troughlike construction of the receiving vessel 18 a receiving aperture 39 is formed, whereby the prongs 22 of the take-up frame run in a direction inclined towards the mounting plate, in order to facilitate the introduction or insertion of instruments, toothbrushes or the like. The toothbrushes 4 or the like are then introduced into the receiving aperture 39 between the rear wall 24 of the receiving vessel 18 and the take-up frame 17, whereby the brush head 5 according to FIG. 1 is braced in the area of the receiving aperture 9, in particular on the tracks 20 of the take-up frame 17 according to FIG. 5.

Figure 10:
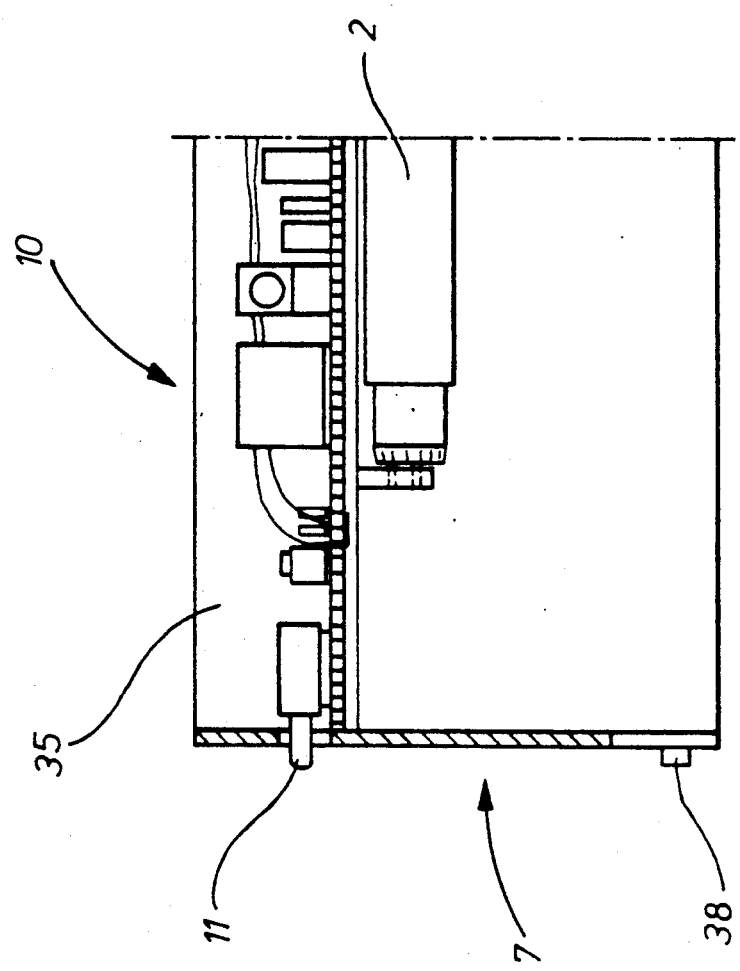
FIG. 10 is a long section of the mounting plate with placement of the electronics in a carrying case.

From the depiction of the cross-section of the apparatus according to FIG. 9 it is clear that upon swinging shut the housing 1 onto the mounting plate 7 over hinge pin 38 according to FIG. 10 an enclosed disinfection chamber is formed, whereby within this disinfection chamber according to FIG. 9 the receiving vessel 18 with the associated take-up frame 17 is arranged. The receiving aperture 39 for instruments, toothbrushes or the like is in this manner accessible from above via the openings 3 in the housing.

The light source 2 is arranged according to FIG. 9 inclusive of the electronics in a receptacle 35 of the mounting plate 7, whereby a light opening 34 is provided in the mounting plate 7, through which UV-radiation is emitted into the housing 1. The receiving vessel 18 with take-up frame 17 and the non-exposed medical instruments, toothbrushes or the like inserted therein are thus located in the manner of a sliding unit or rack where they are very intensely exposed to the light source 2, so that in this manner a shadow-free, advantageous UV-irradiation is effected.

Figure 2:
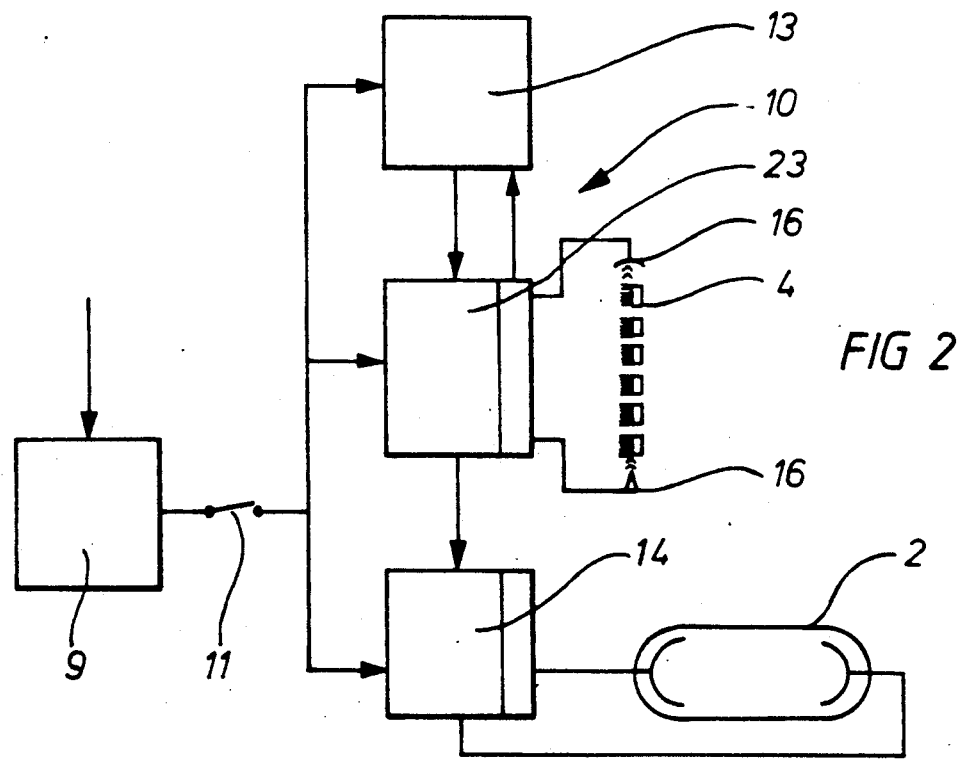
FIG. 2 is a block diagram of the electronics and control device for one embodiment of the inventive apparatus.

In FIG. 9 the sensors 16 are also illustrated, which cover in particular the area beneath the openings 3 in the interior of the housing 1, through which with the initiation of a motion, e.g. by introduction or removal of a toothbrush, the light source 2 is switched on or off by means of the electronics as illustrated in FIG. 2.

FIG. 9 in combination with FIG. 10 further illustrates the switch 11 of FIG. 2, which is activated by a substantial swinging or pivoting of the housing and thereby places the electronics on the supply voltage.

The take-up frame 17 according to FIG. 9 is transparent to UV-radiation, through which an advantageous disinfection chamber is formed within the receiving vessel 18 with reflection of the radiation on the rear wall 24, whereby the closed housing 1 additionally reflects radiation, and in general through the nested arrangement of the receiving vessel 18 within the housing 1 a chamber is formed, wherein the ozone generated by the UV-radiation is suitably collected.

In FIG. 10 the electronics and in particular the control device 10 are arranged on a plate in the receptacle 35 of the mounting plate, the functioning thereof being more clearly illustrated in FIG. 2.

Following from the plug 9 via the switch 10 there is next arranged a counter 13 as well as the sensor electronics 23 and the voltage transformer 14.

The toothbrushes 4 are so held in the receiving aperture 39, that the brushes are directed towards the UV-light source 2. These or other instruments are thereby subjected to the ultraviolet radiation and in this manner disinfected and maintained in a germ-free condition.

The UV-light source 2 is connected to the voltage transformer 14, whereby the supply voltage for the UV-light source with higher frequency is generated in the transformer 14.

The counter 13 is a programmable calculator introduced for monitoring time, which is actuated by placing the apparatus in operation and which turns off the UV-light source after a predetermined period of time, e.g. one hour. FIG. 2 further illustrates the sensor electronics, with the toothbrushes arranged between the sensors 16 comprising an infrared transmitter diode and an infrared receiver diode. Upon a movement of the toothbrushes 4, be it from introduction into the apparatus or removal therefrom, the sensor electronics 23 are actuated and turn the counter 13 on, which in turn actuates the voltage transformer 14 and thereby places the light source 2 into operation.

The procedure is carried out with a UV-light source which generates light with a wavelength of about 253.7 nm. It is, however, also advantageous to use a two-level operating UV-light source, through which ozone is generated in the wavelength range of 180 to 200 nm. Through the irradiation and ozone treatment of the brush heads a compartment-wide disinfection is achieved, in particular in combination with the trough-like construction of the receiving vessel 18 and the multiple reflection of the generated UV-radiation in the region of the enclosure between the receiving vessel 18 and the housing 1, as well as between the rear wall 24 of the mounting plate 7 and the receiving vessel 18.

The apparatus is characterized by a minimal use of current and operates at a low voltage range which is not dangerous for use in bathrooms.

The described apparatus for disinfection and germ-free maintenance of toothbrushes is not contemplated solely for use in private households, but can be used as well in dental practices and in hotel rooms.

Also contemplated as within the scope of the invention is the use of the described apparatus or one similarly constructed for disinfection and germ-free maintenance of other instruments which for example are used in the handling or care of human or animal bodies. In this regard, in addition to medical or dental instruments there is also contemplated hairdressing instruments, such as razor knives and similar instruments, as well as instruments for hand and foot care.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. Apparatus for sterilization of instruments using ultraviolet radiation, comprising:
   a mounting plate provided with side arms;
   a housing provided with openings for insertion of said instruments, said housing being swivel-mounted and receiving the side arms of the mounting plate when closed;
   a light source which generates UV-radiation within said housing;
   a receiving vessel with a take-up frame for the instruments removably inserted in the mounting plate;
   control means for operating said light source; and
   sensor means within said housing for effecting operation of said control means in response to a predetermined stimulus.

2. Apparatus according to claim 1, wherein the mounting plate comprises a wall with an opening for the UV-light source, whereby the receiving vessel with a take-up frame is brought to the light source in the manner of a sliding unit.

3. Apparatus according to claim 1, wherein the side arms of the mounting plate are provided with tracks, in which the receiving vessel may be inserted over corresponding tracks.

4. Apparatus according to claim 1 wherein the receiving vessel is provided with side frames with lateral tracks and a catch, in which the take-up frame is removably inserted.

5. Apparatus according to claim 1, wherein the receiving vessel comprises a highly rifled wall which is combination with the inserted take-up frame forms a receiving aperture for the instruments.

6. Apparatus according to claim 1, wherein the take-up frame is provided on prongs thereof with tracks for introduction of instruments.

7. Apparatus according to claim 1, wherein the base of the receiving vessel is troughlike with an outlet opening.

8. Apparatus according to claim 1, wherein said sensor means comprises at least one transmitter and at least one receiver arranged on the mounting plate in a lateral arrangement in the interior of the housing in the area of the receiving vessel and the openings.

9. Apparatus according to claim 1, wherein the mounting plate comprises a receptacle for receiving electronics including said control means and the UV-light source.

10. Apparatus according to claim 1, wherein a switch is arranged on a side of the mounting plate in an aperture, which switch is actuated upon pivoting of the housing.

11. Apparatus according to claim 9, wherein the control means is provided with a counter which turns off the light source after a predetermined period of time.

12. Apparatus according to claim 9, wherein the control means is provided with a thermostat, which turns the light source off when a predetermined temperature is exceeded and turns it on again when the thermostat registers a temperature below the predetermined temperature.

13. Apparatus according to claim 11, wherein the counter is placed in operation by a manual switching on of the apparatus.

14. Apparatus according to claim 8, wherein sensor scanning is effected in an inductive or capacitative manner.

15. Apparatus according to claim 8, wherein the sensors are responsive to moisture.

16. Apparatus according to claim 8, wherein the sensor means comprises at least one ultrasound transmitter and at least one ultrasound receiver.

17. Apparatus according to claim 1, wherein the light source operates in a two-level manner to generate light of wavelengths of from 180 to 200 nm and of 253.7 nm, whereby ozone is generated in the 180 to 200 nm range.

18. Apparatus according to claim 9, comprising a plug power supply unit, which transforms operating voltage from 220 or 110 volts to from 8 to 12 volts.

19. Apparatus according to claim 1, wherein the take-up frame comprises radiation transparent material.

20. Apparatus according to claim 8, wherein the sensor means comprises at least one infrared transmitter diode and at least one infrared receiver diode for illuminating the interior of the housing in the area of the receiving vessel and the openings.

* * * * *